United States Patent
Martin et al.

(10) Patent No.: US 10,186,174 B2
(45) Date of Patent: Jan. 22, 2019

(54) METHODS AND DEVICES FOR DETERMINING SENSING DEVICE USABILITY

(71) Applicant: Abbott Point of Care Inc., Princeton, NJ (US)

(72) Inventors: Glenn Martin, Ottawa (CA); Tian-Xian Zhao, Ottawa (CA); Stephen L. Snyder, Ottawa (CA)

(73) Assignee: Abbott Point of Care Inc., Princeton, NJ (US)

( * ) Notice: Subject to any disclaimer, the term of this patent is extended or adjusted under 35 U.S.C. 154(b) by 0 days.

(21) Appl. No.: 15/702,887

(22) Filed: Sep. 13, 2017

(65) Prior Publication Data

US 2018/0075782 A1    Mar. 15, 2018

Related U.S. Application Data

(62) Division of application No. 13/538,032, filed on Jun. 29, 2012, now Pat. No. 9,792,838.

(Continued)

(51) Int. Cl.
*G09F 3/00* (2006.01)
*G01N 27/06* (2006.01)
*G01N 27/327* (2006.01)

(52) U.S. Cl.
CPC ........... *G09F 3/0291* (2013.01); *G01N 27/06* (2013.01); *G01N 27/3274* (2013.01)

(58) Field of Classification Search
CPC ......... G09F 3/00; G09F 3/0291; G01N 27/06; G01N 27/327; G01N 27/3274
See application file for complete search history.

(56) References Cited

U.S. PATENT DOCUMENTS

| | | | |
|---|---|---|---|
| 3,922,431 | A | 11/1975 | Radmacher et al. |
| 3,942,467 | A | 3/1976 | Witonsky et al. |

(Continued)

FOREIGN PATENT DOCUMENTS

| | | |
|---|---|---|
| CN | 1427770 | 7/2003 |
| CN | 101815936 | 8/2010 |

(Continued)

OTHER PUBLICATIONS

"Final Office Action" issued in U.S. Appl. No. 13/537,983, dated May 1, 2015, 11 pages.

(Continued)

*Primary Examiner* — Patrick Assouad
*Assistant Examiner* — Haidong Zhang
(74) *Attorney, Agent, or Firm* — Kilpatrick Townsend & Stockton LLP (57) ABSTRACT

Methods and devices for determining device usability, e.g., for point of care assay devices. In one embodiment, the invention is to a method of determining device usability in a sensing device, including the steps of: providing a device comprising a first electrical pad; a second electrical pad; and a first polymer layer contacting at least a portion of the first and the second electrical pads and a second polymer layer contacting the first polymer layer and not the first and second electrical pads; applying a potential across the first and the second electrical pads; measuring an electrical property associated with the first and the second polymer layers; and determining whether the measured electrical property associated with the first and the second polymer layers has exceeded a threshold level associated with the device usability.

14 Claims, 3 Drawing Sheets

Related U.S. Application Data (60) Provisional application No. 61/540,026, filed on Sep. 28, 2011, provisional application No. 61/503,234, filed on Jun. 30, 2011.

(56) References Cited

U.S. PATENT DOCUMENTS

| | | | |
|---|---|---|---|
| 3,983,527 | A | 9/1976 | Ohsato et al. |
| 4,059,406 | A | 11/1977 | Fleet et al. |
| 5,096,669 | A | 3/1992 | Lauks et al. |
| 5,209,931 | A * | 5/1993 | Levin ............... A01N 25/10 424/405 |
| 5,273,640 | A | 12/1993 | Kusanagi et al. |
| 5,554,339 | A | 9/1996 | Cozzette et al. |
| 6,063,486 | A | 5/2000 | Kobayashi et al. |
| 6,158,381 | A | 12/2000 | Bray |
| 6,544,925 | B1 | 4/2003 | Prusik et al. |
| 6,629,057 | B2 | 9/2003 | Zweig et al. |
| 7,418,285 | B2 | 8/2008 | Ghesquiere et al. |
| 7,612,325 | B1 | 11/2009 | Watkins, Jr. et al. |
| 7,723,099 | B2 | 5/2010 | Miller et al. |
| 8,835,180 | B2 | 9/2014 | Gryska et al. |
| 2003/0139903 | A1 | 7/2003 | Zweig et al. |
| 2003/0148530 | A1 | 8/2003 | Lauks et al. |
| 2004/0158137 | A1 | 8/2004 | Eppstein et al. |
| 2004/0256227 | A1 | 12/2004 | Shin et al. |
| 2006/0214312 | A1 | 9/2006 | Wu et al. |
| 2007/0132542 | A1 | 6/2007 | Beck et al. |
| 2007/0166831 | A1 | 7/2007 | Watkins et al. |
| 2008/0145277 | A1 | 6/2008 | Wohland et al. |
| 2009/0022630 | A1 | 1/2009 | Hoenes et al. |
| 2009/0056644 | A1 | 3/2009 | Phillips et al. |
| 2009/0119047 | A1 | 5/2009 | Zelin et al. |
| 2009/0159442 | A1 | 6/2009 | Collier et al. |
| 2009/0182244 | A1 | 7/2009 | Hoenes et al. |
| 2009/0184004 | A1 * | 7/2009 | Chatelier ............ G01N 27/3274 205/777.5 |
| 2010/0206749 | A1 | 8/2010 | Choi et al. |
| 2010/0270175 | A1 * | 10/2010 | Pei ......................... C12Q 1/006 205/777.5 |
| 2011/0105613 | A1 | 5/2011 | Reiner et al. |
| 2011/0155043 | A1 | 6/2011 | Haarer et al. |
| 2011/0155589 | A1 | 6/2011 | Chatelier et al. |
| 2012/0108694 | A1 | 5/2012 | Malet et al. |
| 2013/0000378 | A1 | 1/2013 | Martin et al. |
| 2013/0002265 | A1 | 1/2013 | Martin et al. |
| 2013/0002278 | A1 | 1/2013 | Martin et al. |
| 2013/0002279 | A1 | 1/2013 | Martin et al. |
| 2016/0054248 | A1 | 2/2016 | Martin et al. |
| 2016/0313273 | A1 | 10/2016 | Martin et al. |

FOREIGN PATENT DOCUMENTS

| | | |
|---|---|---|
| CN | 103748458 | 4/2014 |
| CN | 103748459 | 4/2014 |
| CN | 103748458 | 3/2016 |
| EP | 2098857 | 9/2009 |
| EP | 2726859 | 5/2014 |
| EP | 2726860 | 5/2014 |
| WO | 2009036429 | 3/2009 |
| WO | 2009156285 | 12/2009 |
| WO | 2010086574 | 8/2010 |
| WO | 2013003705 | 1/2013 |
| WO | 2013003709 | 1/2013 |
| WO | 2013003711 | 1/2013 |
| WO | 2013003718 | 1/2013 |

OTHER PUBLICATIONS

"Non-Final Office Action" issued in U.S. Appl. No. 13/537,983, dated Jul. 31, 2014, 13 pages.
"Notice of Allowance" issued in U.S. Appl. No. 13/537,983, dated Aug. 10, 2015, 8 pages.
"Advisory Action" issued in U.S. Appl. No. 13/538,032, dated Jun. 9, 2017, 4 pages.
"Final Office Action" issued in U.S. Appl. No. 13/538,032, dated Feb. 16, 2017, 13 pages.
"Non-Final Office Action" issued in U.S. Appl. No. 13/538,032, dated Jun. 30, 2016, 7 pages.
"Notice of Allowance" issued in U.S. Appl. No. 13/538,032, dated Jul. 5, 2017, 8 pages.
"Non-Final Office Action" issued in U.S. Appl. No. 13/538,148, dated Mar. 20, 2015, 20 pages.
"Notice of Allowance", issued in U.S. Appl. No. 13/538,148, dated Aug. 24, 2015, 11 pages.
"Final Office Action", issued in U.S. Appl. No. 13/538,218, dated Apr. 15, 2015, 14 pages.
"Non-Final Office Action" issued in U.S. Appl. No. 13/538,218, dated Sep. 23, 2015, 10 pages.
"Non-Final Office Action" issued in U.S. Appl. No. 13/538,218 dated Oct. 2, 2014, 12 pages.
"Notice of Allowance" issued in U.S. Appl. No. 13/538,218, dated May 16, 2016, 5 pages.
"Non-Final Office Action" issued in U.S. Appl. No. 14/927,508, dated Jan. 29, 2016, 24 pages.
"Notice of Allowance" issued in U.S. Appl. No. 14/927,508, dated May 2, 2016, 8 pages.
"Non-Final Office Action" issued in U.S. Appl. No. 15/203,020, dated Aug. 2, 2016, 15 pages.
"Notice of Allowance" issued in U.S. Appl. No. 15/203,020, dated Nov. 25, 2016, 8 pages.
"I-STAT System Manual", Abbott Point of Care, 2004.
"Office Action" issued in CN201280039926.0, dated Oct. 13, 2014, 16 pages.
"Office Action" issued in CN201280039926.0, dated Jun. 26, 2015, 9 pages.
"Office Action" issued in CN201280039929.4, dated Sep. 22, 2014, 14 pages.
Heller et al., "Electrochemical Glucose Sensors and Their Applications in Diabetes Management", Chemical Reviews, vol. 108, Issue 7, Jul. 1, 2008, pp. 2482-2505.
"International Preliminary Report on Patentability" issued in PCT/US2012/044898, dated Jan. 16, 2014, 8 pages.
"International Search Report and Written Opinion" issued in PCT/US2012/044898, dated Oct. 5, 2012, 10 pages.
"International Preliminary Report on Patentability" issued in PCT/US2012/044905, dated Jan. 16, 2014, 7 pages.
"International Search Report and Written Opinion", issued in PCT/US2012/044905, dated Oct. 5, 2012, 9 pages.
"International Preliminary Report on Patentability", issued in PCT/US2012/044909, dated Jan. 16, 2014, 8 pages.
"International Search Report and Written Opinion", issued in PCT/US2012/044909, dated Oct. 5, 2012, 10 pages.
"International Preliminary Report on Patentability", issued in PCT/US2012/044919, dated Jan. 16, 2014, 8 pages.
"International Search Report and Written Opinion", issued in PCT/US2012/044919, dated Oct. 5, 2012, 10 pages.

\* cited by examiner

METHODS AND DEVICES FOR DETERMINING SENSING DEVICE USABILITY

CROSS REFERENCE TO RELATED APPLICATIONS

This application is a divisional of U.S. Ser. No. 13/538,032, filed Jun. 29, 2012, which claims priority to U.S. Provisional Application No. 61/540,026 filed Sep. 28, 2011 and to U.S. Provisional Application No. 61/503,234 filed Jun. 30, 2011, the entireties of which are incorporated herein by reference.

FIELD OF THE INVENTION

The present invention relates to methods and devices for determining sensing device usability. In particular, the methods and devices can be used for determining device usability through application of a potential across two electrical pads and two or more polymer layers there between and measuring an electrical property of the polymer layers to determine whether a device has exceeded a threshold level associated with device usability.

BACKGROUND OF THE INVENTION

A multitude of laboratory tests for analytes of interest are performed on biological samples for diagnosis, screening, disease staging, forensic analysis, pregnancy testing and drug testing, among others. While a few qualitative tests, such as glucose, prothrombin, and pregnancy tests, have been reduced to simple kits for a patient's home use, the majority of quantitative tests still require the expertise of trained technicians in a laboratory setting using sophisticated instruments. Laboratory testing increases the cost of analysis and delays the patient's or clinician's receipt of the results. In many circumstances, this delay can be detrimental to the patient's condition or prognosis, such as for example the analysis of markers indicating myocardial infarction and heart failure. In these and similar critical situations, it is advantageous to perform such analyses at the point-of-care, accurately, inexpensively and with minimal delay.

Point-of-care sample analysis systems are generally based on a reusable reading apparatus that performs sample tests using a disposable device (e.g., a cartridge or strip) that contains analytical elements (e.g., electrodes or optics for sensing analytes such as, for example, pH, oxygen, or glucose). The disposable device can optionally include fluidic elements (e.g., conduits for receiving and delivering the sample to the electrodes or optics), calibrant elements (e.g., fluids for standardizing the electrodes with a known concentration of the analyte), and dyes with known extinction coefficients for standardizing optics.

Point-of-care sample testing systems eliminate the time-consuming need to send a sample to a central laboratory for testing. Point-of-care sample testing systems allow a user e.g. a nurse and physician, at the bedside of a patient, to obtain reliable, quantitative, analytical results, comparable in quality to that which would be obtained in a laboratory. In operation, the user may select a device with the required panel of tests (e.g., electrolytes, metabolites, cardiac markers and the like), draw a sample, dispense it into the device, optionally seal the device, and insert the device into the reading apparatus to communicate the data to an LIS/HIS for analysis. An example of such a system is the i-STAT® system sold by Abbott Point-of-Care, Inc., Princeton, N.J., USA. The i-STAT® portable blood analysis system typically comprises Wi-Fi-enabled reader instruments that work in conjunction with single-use blood testing cartridges that contain sensors for various analytes. For further information on the i-STAT® portable blood analysis system, see http://www.abbottpointofcare.com/.

Analyzers, such as a self-contained disposable sensing device or cartridge and a reader or instrument, are further described in now expired U.S. Pat. No. 5,096,669 to Lauks, et al., the entirety of which is incorporated herein by reference. In operation, a fluid sample to be measured is drawn into a device and the device is inserted into the reader through a slotted opening. Data generated from measurements performed by the reader may be output to a display and/or other output device, such as a printer, or, as described in greater detail below, via a wireless network connection. The disposable device may contain sensing arrays and several cavities and conduits that perform sample collection, provide reagents for use in measurement and sensor calibration, and transport fluids to and from the sensors. Optionally, reagents may be mixed into the sample for testing. Sensing arrays in the device measure the specific chemical species in the fluid sample being tested. The electrochemical sensors are exposed to and react with the fluid sample to be measured generating electrical currents and potentials indicative of the measurements being performed. The electrochemical sensors may be constructed dry and when the calibrant fluid flows over the electrochemical sensors, the sensors easily "wet up" and are operational and stable for calibration and composition measurements. These characteristics provide many packaging and storage advantages, including a long shelf life. Each of the sensing arrays may comprise an array of conventional electrical contacts, an array of electrochemical sensors, and circuitry for connecting individual sensors to individual contacts. The electrical signals are communicated to a reader enabled to perform calculations and to display data, such as the concentration of the results of the measurement.

Although the particular order in which the sampling and analytical steps occur may vary between different point-of-care systems and providers, the objective of providing rapid sample test results in close proximity to a patient remains. The reading apparatus (e.g., i-STAT® or other wireless analyzer) may then perform a test cycle (i.e., all the other analytical steps required to perform the tests). Such simplicity gives the physician quicker insight into a patient's physiological status and, by reducing the time for diagnosis, enables a quicker decision by the physician on the appropriate treatment, thus enhancing the likelihood of a successful patient treatment.

In the emergency room and other acute-care locations within a hospital, the types of sample tests required for individual patients can vary widely. Thus, point-of-care systems generally offer a range of disposable devices configured to perform different sample tests, or combinations of such tests. For example, for blood analysis devices, in addition to traditional blood tests, including oxygen, carbon dioxide, pH, potassium, sodium, magnesium, calcium, chloride, phosphate, hematocrit, glucose, urea (e.g., BUN), creatinine and liver enzymes, other tests may include, for example, prothrombin time (PT), activated clotting time (ACT), activated partial thromboplastin time (APTT), troponin, creatine kinase MB (CKMB), and lactate. Although devices typically contain between one and ten tests, it will be appreciated by persons of ordinary skill in the art that any number of tests may be contained in a device.

A given hospital may use numerous different types of test devices and test instruments at multiple point-of-care testing locations within the hospital. These locations can include, for example, an emergency room (ER), a critical care unit (CCU), a pediatric intensive care unit (PICU), an intensive care unit (ICU), a renal dialysis unit (RDU), an operating room (OR), a cardiovascular operating room (CVOR), general wards (GW), and the like. Other non-hospital-based locations where medical care is delivered, include, for example, MASH units, nursing homes, and cruise, commercial, and military ships.

In some cases, cartridges have a shelf life, which may vary widely depending on the specific cartridge as well as upon storage conditions. For example, some cartridges may have a shelf life of about six to about nine months when refrigerated, but a much more limited shelf life, e.g., about two weeks at room temperature, or, more specifically, about ten weeks at up to about 30° C. As a result, hospitals typically store cartridges at a central refrigerated location, and deliver cartridges to specific locations, as demand requires. These locations can include, for example, an emergency room (ER), critical care unit (CCU), pediatric intensive care unit (PICU), intensive care unit (ICU), renal dialysis unit (RDU), operating room (OR), cardiovascular operating room (CVOR) and general wards (GW). These locations may or may not have available refrigerated storage, and this will influence product lifetime and, as a result, the inventory they will hold. Further complicating device management is the fact that a given user, such as a hospital, may use multiple types of cartridges, each having a different shelf life. Alternatively, the user may be a physician's office laboratory or visiting nurse service. However, the need to ensure quality remains the same.

U.S. Patent Appl. No. US 2009/0119047 to Zelin et al., the entirety of which is incorporated herein by reference, discloses an improved quality assurance system and method for point-of-care testing. It provides quality assurance for laboratory quality tests performed by a blood analysis system at the point of patient care without the need for running liquid-based quality control materials on the analysis system. Quality assurance of a quantitative physiological sample test system is performed without using a quality control sample by monitoring the thermal and temporal stress of a component used with the test system. Alert information is generated that indicates that the component has failed quality assurance when the thermal and temporal stress exceeds a predetermined thermal-temporal stress threshold.

U.S. Pat. No. 7,612,325 to Watkins Jr., et al., the entirety of which is incorporated herein by reference, discloses electrical sensor for monitoring degradation of products from environmental stressors and describes an environmental degradation sensor for environmentally sensitive products such as food, pharmaceuticals or cosmetic products provides the degraded state and estimated remaining life of the product. The sensor is made of a polymeric matrix and conductive filler. A control agent, selected to adjust a reaction rate of the sensor to environmental conditions, allows correlation of an electrical property of the sensor to a degraded state of the product.

In general, the principles of operation for existing types of time/temperature indicators can be categorized as physical, chemical and electrical. Examples of physical and chemical methods include color change of polymeric materials, chemical reactions of two elements, physical masking of a marker, melting of a temperature sensitive material and the like.

However, the use of many existing indicators adds significant cost and complexity to the devices they are intended to monitor. This is a particularly apparent issue for single-use blood testing cartridges and electrochemical strip devices, e.g., glucose blood testing strips used by diabetics. Consequently, the need remains for improved low cost time-temperature indicators that are amenable to direct integration into a device manufacturing workflow. The need also exists for methods and devices for correcting signals in such devices.

SUMMARY OF THE INVENTION

The present invention relates to sensing devices having first and second electrical pads and having a first polymer layer and a second polymer layer disposed there between. Preferably, the first polymer layer has a different conductivity and impedance than the second polymer layer. Over time and/or at elevated temperatures, the polymer layers may migrate or diffuse into one another causing an increase in conductivity (and reduction in resistivity) between the two electrical pads. As a result, an electrical property associated with the first and second electrical pads may be correlated to device usability and/or may be used to derive a correction factor that may be applied to a device signal to determine a corrected device signal.

In one embodiment, for example, the invention is to a method of determining device usability, comprising: providing a device comprising a first electrical pad; a second electrical pad; and a first polymer layer contacting at least a portion of the first and the second electrical pads, e.g., contact pads. The device also includes a second polymer layer contacting the first polymer layer and not the first and the second electrical pads. The method includes applying a potential across the first and the second electrical pads; measuring an electrical property associated with the first and the second polymer layers; and determining whether the measured electrical property associated with the first and the second polymer layers has exceeded a threshold level associated with the device usability. The first polymer layer may be a continuous polymer layer.

In another embodiment, the invention is to a device having a usability threshold comprising a first electrical pad; a second electrical pad; a first polymer layer electrically contacting at least a portion of the first and the second electrical pads; and a second polymer layer contacting the first polymer layer but not contacting the first and the second electrical pads. The first and the second polymer layers have an electrical property associated with the device usability threshold.

In another embodiment, the invention is to a device comprising a sensor; a first polymer layer formed on a surface of the device; a second polymer layer in contact with the first polymer layer, e.g., formed on the first polymer layer; a first electrical pad; and a second electrical pad. The surface comprises the first and the second electrical pads positioned adjacent to one another and a space there between. The first polymer layer covers at least a portion of the first and the second electrical pads and at least a portion of the space between the layers, and the second polymer layer contacts the first polymer layer but not the first and the second electrical pads. In the device, a preselected potential or potential cycle is applied to the first and the second electrical pads and an impedance or current associated with the first and the second polymer layers is measured. The measured impedance or current is converted to a value indicative of an average shelf life time remaining for other devices from a same manufacturing lot of the device.

In yet another embodiment, the invention is to a method of determining device usability comprising providing a device comprising a first electrical pad; a second electrical pad; a first polymer layer contacting at least a portion of the first and the second electrical pads; and a second polymer layer contacting the first polymer layer but not the first and the second electrical pads. A potential is applied across the first and the second electrical pads, and an electrical property associated with the first and the second polymer layers is measured. A correction factor associated with the measured electrical property is determined, which is applied to a signal generated by a sensor to produce a corrected signal.

In preferred embodiments, the first polymer layer and/or the second polymer layer comprises a polymer matrix, a plasticizer and an organic salt. For example, the first polymer layer and/or the second polymer layer may comprise from 20 to 40 wt. % polymer matrix. The polymer matrix may comprise a polymer selected from the group consisting of polyvinyl chloride, polyurethane, polyvinylacetate, carboxylated PVC, hydroxylated PVC and polydimethyl siloxane. The first polymer layer optionally comprises from 60 to 80% plasticizer, which may be selected from the group consisting of trioctyl phosphate (TOP), nitrophenyloctyl ether (NPOE), bisethylhexylsebacate (BEHS), trimethyl trimellitate (TMTT), dioctyl adipate (DOA) and diisobutyl phthalate (DIBP). The first polymer layer and/or the second polymer layer may comprise from 0.1 to 10 wt. % of an organic or inorganic salt, e.g., a salt selected from the group consisting of quaternary ammonium tetrakis phenylborate, dodecyl sulfosuccinate, lauryl sulfate, alkyl ether phosphates, benzylkonium, cetylpyrdinium dodecyl sulfosuccinate, lauryl sulfate, alkyl ether phosphates, tetramethylammonium, benzylkonium, cetylpyrdinium, an iodide, a bromide, a perchlorate, a zwitterionic compound, cocamidopropyl hydroxysultaine and quaternary ammonium borate.

The configuration and shape of the first polymer layer and/or the second polymer layer may vary widely, but in one embodiment, the continuous first polymer layer is substantially circular, preferably domed, and has a diameter of from about 20 μm to about 2 mm. The device may further comprise a boundary structure for controlling the spreading of a dispensed first polymer layer precursor and/or the second polymer layer precursor to a predetermined region of the device, e.g., a ring intersecting the first and second electrical contact pads. The first and second pads optionally are separated by a distance of from about 10 μm to about 2 mm.

Another aspect of the invention is to a method of determining device usability, comprising: providing a device comprising a first electrical pad; a second electrical pad; and a first polymer layer contacting at least a portion of the first electrical pad, and a second polymer layer contacting the at least a portion of the second electrical pad and at least a portion of the first polymer layer. A potential is applied across the first and the second electrical pads; an electrical property associated with the first and the second polymer layers is measured and it is determined whether the measured electrical property associated with the first and the second polymer layers has exceeded a threshold level associated with the device usability.

Another embodiment of the invention is to a device having a usability threshold comprising a first electrical pad; a second electrical pad; a first polymer layer contacting at least a portion of the first electrical pad; and a second polymer layer contacting at least a portion of the second electrical pad and at least a portion of the first polymer layer. The first and the second polymer layers have an electrical property associated with the device usability threshold.

In a further embodiment, the invention is to a device comprising a sensor; a first polymer layer formed on a surface of the device; a second polymer layer formed on the surface of the device; a first electrical pad; and a second electrical pad. The surface comprises the first and the second electrical pads positioned adjacent to one another and a space there between. The first polymer layer covers at least a portion of the first electrical pad and at least a portion of the space between the pads; the second polymer layer contacts at least a portion of the second electrical pad, at least a portion of the first polymer layer, and at least a portion of the space therebetween. A preselected potential or potential cycle is applied to the first and the second electrical pads and impedance or current associated with the first and the second polymer layers is measured. The measured impedance or current is converted to a value indicative of an average shelf life time remaining for other devices from a same manufacturing lot of the device. The surface of the device may be substantially planar.

In another embodiment, the invention is to a method of determining device usability comprising providing a device comprising a first electrical pad; a second electrical pad; and a first polymer layer contacting at least a portion of the first electrical pad and a second polymer layer contacting at least a portion of the second electrical pad and at least a portion of the first polymer layer; applying a potential across the first and the second electrical pads; measuring an electrical property associated with the first and the second polymer layers; determining a correction factor associated with the measured electrical property; and applying the correction factor to a signal generated by a sensor to produce a corrected signal. The devices of the invention typically have been exposed to different environmental conditions, e.g., time since manufacture, temperature, ambient conditions or a combination thereof.

In one aspect, the potential or potential cycle comprises a sigmoidal potential cycle, a fixed applied potential, a sequence of fixed applied potential steps, or a combination thereof. The potential optionally comprises a potential cycle that is applied at a predetermined frequency in the range of about 1 Hz to about 100000 Hz. The methods of the invention optionally include a step of inserting the device into an analyzer configured to determine whether the measured electrical property associated with the first and second polymer layers has exceeded a threshold level associated with the device usability.

The correction factor preferably is applied to a sensor selected from the group consisting of a pH sensor, oxygen sensor, carbon dioxide sensor, hematocrit sensor, glucose sensor, lactate sensor, creatinine sensor, sodium sensor, bilirubin, potassium sensor, magnesium sensor, calcium sensor, chloride sensor, inorganic phosphate sensor, liver enzyme sensor, BNP sensor, troponin sensor, BUN sensor, CKMB sensor, NGAL sensor, TSH sensor, D-dimer sensor, PSA sensor, PTH sensor, cholesterol sensor, ALT sensor, AST sensor, prothrombin sensor, APTT sensor, ACT sensor, galectin sensor, CG sensor, and combinations thereof.

The correction factor preferably is selected from the group consisting of an amperometric correction value, a potentiometric correction value, a coulombic correction value and a conductivity correction value.

BRIEF DESCRIPTION OF THE DRAWINGS

The present invention will be better understood in view of the appended non-limiting figures, in which.

DETAILED DESCRIPTION OF THE INVENTION

The present invention is best understood in the context of point-of-care blood analysis systems. For example, the shelf life of an i-STAT® cartridge (see the i-STAT® system made by Abbott Point of Care, Princeton, N.J., USA) is typically indicated by a refrigeration expiration date and a room temperature shelf life that are provided on the product packaging, e.g., on a fluid-containing pouch thereof. The refrigeration expiration date defines the length of time that the cartridge may be stored under refrigerated conditions after manufacture, e.g., at about 5° C. Depending on the specific device, the refrigeration expiration date may be about three months, about six months, about nine months or about one year after the date of manufacture. The room temperature shelf life defines the length of time that the cartridge may be stored under room temperature (ambient, e.g., 25° C.) conditions after a cartridge or a box of cartridges is removed from refrigeration conditions, i.e., removed from a refrigerator. The room temperature shelf life should not be allowed to exceed the refrigeration expiration date. The room temperature shelf life is typically about from two to nine weeks, depending on cartridge type. In practice, the room temperature expiration date is calculated from the room temperature shelf life and is written on the box by the user at the time of removal from the fridge. Thus, when a box of cartridges is taken out of the refrigerator, the user typically counts the number of days or months to determine the room temperature expiration date, verifies that the room temperature expiration date does not exceed the refrigeration expiration date printed on the box or cartridge, and writes the room temperature expiration date down on the box. Furthermore, when a cartridge is to be used, the end user again checks the expiry dates. This process lends itself to potential user error in either or both calculating the refrigeration expiration date and/or verifying that the refrigeration expiration date has not been passed. The present invention is intended to facilitate determining the suitability of the cartridge for use, i.e., the non-expiration of the shelf life, automatically taking into consideration the age of the device as well as the environment, e.g., temperature, under which the device has been stored. Thus, the user is relieved of this task and the opportunity for a user-induced error is diminished.

While there are several time-temperature or shelf life indicators that are known in the art, it is highly desirable to keep the cost and complexity of the device to a minimum. In the present invention this is achieved by providing (or modifying) a pair of electrical contact pads. Many analytical systems employ electrical or electrochemical principles and will already have such electrical contact pads as part of the device. Consequently, their use adds no cost as they are present and necessary for other functions, e.g., are used in analyte detection or in device calibration. The pads are desirably modified so that they can act as time-temperature or shelf life indicators (TTI) while still fulfilling their intended purpose, typically analyte detection or device calibration. Thus, the time-temperature indicator function of the invention should also be conducted without diminishing the ability or performance of the contact pads for their primary purpose, e.g., signal transmission in analyte sensing or device calibration. It is also contemplated, however, that the electrical contact pads that are used for time/temperature indication according to some embodiments may be separately provided specifically for performing the role of the TTI, and do not provide any other role, e.g., in analyte sensing or device calibration. In this latter aspect, separate contact pads optionally may be provided for analyte detection and/or device calibration.

The present invention was in part stimulated by the observation that the electrical resistance of some prototype ion sensor membrane structures was found to change after being incubated at an elevated temperature for periods of time. The present invention is thus based on the changing electrical properties, e.g., current flow, resistance and the like, of a connecting material, e.g., connecting layer, comprising at least two polymers, preferably at least two polymer layers, or the like, that is positioned between and preferably in electrical contact with two adjacent contact pads. In one aspect of the invention, at least two polymers are comprised of different materials, preferably having different conductivities, and are referred to as a "first TTI material" and "a second TTI material." Where the TTI materials comprise polymer layers, they are referred to herein as a "first polymer layer" and a "second polymer layer," respectively. A connecting material comprising such two different materials is referred to herein as a heterogeneous connecting material or, where the two different materials are in the form of layers, a heterogeneous connecting layer or simply a heterogeneous layer.

The first and second TTI materials are preferably responsive to the integral of varying temperature (or other environmental conditions) over time such that this gives rise to a predictable change of their electrical properties. In accordance with aspects of the invention, a TTI relationship between thermal exposure (or other environmental conditions) and change in electrical property may be established such that the electrical property e.g., conductivity or resistance, of the heterogeneous layer depends upon an amount of electrolyte in the heterogeneous layer, e.g., the conductivity or resistance of the heterogeneous layer may depend upon the wt % of the conductive salt in the heterogeneous layer. For instance, at 10 Hz, a 2% conductive salt, e.g., an electrolyte, may provide a conductance of 0.025 and a 5% conductive salt may provide a conductance of 0.052 (Sm-1) using a mixture of 66% trioctyl phosphate (TOP) and 34% polyvinylchloride (PVC).

Devices suitable for use in the present invention include, but are not limited to, point-of-care devices such as those disclosed in U.S. Pat. No. 7,723,099, the entirety of which is incorporated herein by reference. The devices preferably comprise a first electrical pad and a second electrical pad in contact with a sensor. As used herein, the term "electrical pad" refers to a location wherein electricity may be applied to the device. The electrical pads of the present invention may comprise, for example, a metal contact comprising gold, silver, a combination thereof or another metal. Suitable sensors for use with the present invention include, but are not limited to, electrochemical sensors, amperometric sensors, potentiometric sensors and conductimetric sensors.

The present invention will be specifically described in the context of an i-STAT cartridge that employs two adjacent hematocrit (Hct) electrode pads, or an Hct pad adjacent to an amperometric sensor pad. Note that, for example, a hematocrit sensor can be used for fluidic integrity checking. Each electrode (or bar) terminates in a contact pad, which is used to make contact with the connector in an i-STAT cartridge reader. Features of the connectors are described in jointly owned U.S. Pat. No. 4,954,087, the entirety of which is incorporated herein by reference. As indicated above, the primary functions of integrity checking and hematocrit measurement should not be affected by the additional use of the pads as part of the TTI.

In a first embodiment, the present invention relates to a method or methods for determining device usability with a TTI. In one embodiment, the method comprises the steps of providing a device comprising a first electrical pad, a second electrical pad, and a heterogeneous layer comprising a first TTI material, preferably a first polymer layer, and a second TTI material, preferably a second polymer layer. The first TTI material preferably is more conductive than the second TTI material, or vice versa. The heterogeneous layer electrically contacts at least a portion of the first and second electrical pads. Preferably, the first and second TTI materials are selected such that they are compatible with one another in the sense that over time and/or at elevated temperatures, the two TTI materials migrate or diffuse into one another causing an increase in conductivity (or reduction in resistivity) between the first and second electrical pads. Prior to or at the time of device use, a potential is applied across the first and second electrical pads and an electrical property associated with the first and second TTI materials is measured. It is then determined whether the measured electrical property associated with the first and second TTI materials has exceeded a threshold level associated with device usability.

Figure 1A:
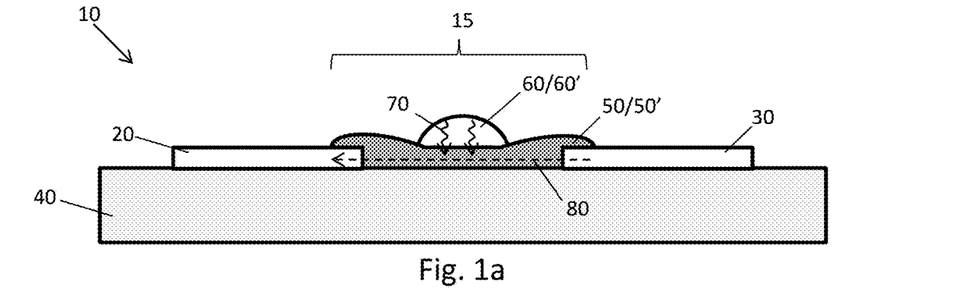
FIGS. 1a and 1b show side and plane views, respectively, of a time-temperature indicator (TTI) device in accordance with one embodiment of the invention.
Figure 1B:
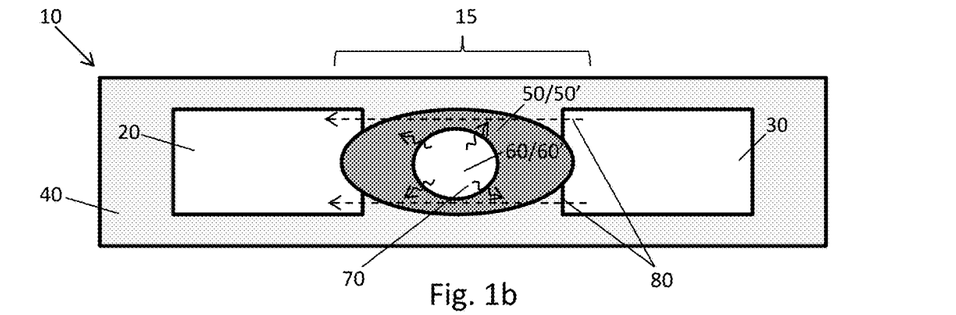

In some embodiments, as shown in FIGS. 1a and 1b, the TTI device 10 for determining device usability comprises a heterogeneous layer 15 formed in electrical contact with contact pads 20 and 30. The contact pads 20 and 30 may further be in electrical contact with a substrate or base 40 (optionally a sensor). In accordance with aspects of the invention, the heterogeneous layer 15 may be formed comprising a first TTI material 50 and a second TTI material 60.

The first TTI material 50 may be formed by depositing a first TTI material precursor 50' between the contact pads 20 and 30. In one aspect, the first TTI material precursor 50' is deposited in contact with at least a portion of both contact pad 20 and contact pad 30. The first TTI material 50 may comprise a polymer layer, preferably a continuous polymer layer, and the first TTI material precursor 50' may comprise a polymer layer precursor. For example, the first TTI material 50 may be formed by depositing, e.g., printing, the TTI material precursor 50', e.g., polymer layer precursor, between and preferably overlapping at least a portion of the contact pads 20 and 30, e.g., an amperometric contact pad and a Hct pad or two Hct pads. After deposition of the precursor, the material is preferably dried or cured (e.g., with heat and/or UV radiation) to form the first TTI material 50.

The second TTI material 60 may be formed by depositing a second TTI material precursor 60' onto the first TTI material 50 (after drying or curing) or onto the first TTI material precursor 50' (prior to drying or curing). Preferably, the second TTI material precursor 60' is deposited without contacting contact pads 20 and 30. The second TTI material 60 may comprise a polymer layer and the second TTI material precursor 60' may comprise a polymer layer precursor. For example, the second TTI material 60 may be formed by depositing, e.g., printing, the second TTI material precursor 60', e.g., polymer layer precursor, onto the first material precursor 50' so that the TTI material precursor 60' does not contact either contact pad 20 or contact pad 30, e.g., an amperometric contact pad and a Hct pad or two Hct pads, but the second TTI material precursor 60' contacts either the first TTI material precursor 50' or the first TTI material 50 (after drying or curing).

The first TTI material precursor 50' and the second TTI material precursor 60' are preferably treated, e.g., with heat or other radiation, dried and/or cured, to form the first TTI material 50 and the second TTI material 60, respectively, and forming the heterogeneous layer 15, in a region between the contact pads 20 and 30, and preferably overlapping the contact pads 20 and 30. The precursors may be treated separately or together. Preferably, the second TTI material precursor is deposited on the first TTI material, i.e., after drying or curing of the first TTI material precursor, in order to minimize migration or diffusion of the two TTI materials during device manufacture. Alternatively, the precursors may be sequentially deposited and treated in a single treating step after they have both been deposited.

In preferred embodiments, one of the first TTI material or the second TTI material is substantially non-conductive, and the other of the first TTI material or the second TTI material includes a conductive material. In the embodiment shown in FIGS. 1a and 1b, it is preferred that the second TTI material 60 is more conductive than the first TTI material 50. Thus, for example, the first TTI material 50 may be substantially non-conductive, comprising a polymer layer that comprises a polymer matrix and a plasticizer and is substantially free of any conductive materials, e.g., salts. The second TTI material 60 may similarly comprise a polymer matrix and a plasticizer, but also preferably comprises a conductive material, e.g., an organic or inorganic salt. Of course, in an alternative embodiment, the first TTI material may be more conductive than the second TTI material. In some exemplary embodiments, the two TTI materials have a difference in conductivity of at least $2.0 \times 10^{-2}$ S·m$^{-1}$, e.g., at least $1.7 \times 10^{-2}$ S·m$^{-1}$ or at least $1.4 \times 10^{-2}$ S·m$^{-1}$. For example, the first TTI material may have a conductivity of from $1.0 \times 10^{-5}$ to $2.0 \times 10^{-6}$ S·m$^{-1}$, from $2.0 \times 10^{-5}$ to $5.0 \times 10^{-6}$ S·m$^{-1}$ or from $2.0 \times 10^{-6}$ to $5.0 \times 10^{-7}$ S·m$^{-1}$, and the second TTI material may have a conductivity of from $1.0 \times 10^{-1}$ to $2.0 \times 10^{-2}$ S·m$^{-1}$, e.g., from $5.0 \times 10^{-2}$ to $1.7 \times 10^{-2}$ S·m$^{-1}$ or from $3.3 \times 10^{-2}$ to $1.4 \times 10^{-2}$ S·m$^{-1}$ in a frequency range of 1-10 Hz.

Each of the polymer layers may comprise from 10 to 60 wt. %, e.g., from 20 to 40 wt. %, polymer matrix, and from 40 to 90 wt %, e.g., from 60 to 80 wt. %, plasticizer. The polymer matrix optionally is selected from the group consisting of polyvinylchloride (PVC), polyurethane (PU), polyvinylacetate, carboxylated PVC, hydroxylated PVC and polydimethylsiloxane (silicon rubber). The plasticizer is optionally selected from the group consisting of trioctyl phosphate (TOP), nitrophenyloctyl ether (NPOE), bisethylhexylsebacate (BEHS), trimethyl trimellitate (TMTT), dioctyl adipate (DOA) and diisobutyl phthalate (DIBP).

The specific composition of the TTI material precursors, e.g., polymer layer precursors, that are used to form the TTI materials, e.g., first and second polymer layers, may vary widely. In an exemplary embodiment, either TTI material precursor comprises the polymer matrix and the plasticizer, as discussed above, but preferably further comprises a carrier medium (e.g., solvent) for imparting the desired physical properties for deposition thereof as well as solubilizing the polymer contained therein. In another embodiment, either of the TTI material precursors comprises a monomer and an initiator, and polymerization may occur after deposition of the TTI material precursor 50' between the contact pads 20 and 30 of the sensor 40, e.g., through free radical polymerization, optionally with the application of UV radiation.

As indicated above, one of the first and second TTI materials should be more conductive than the other. As a result, the TTI material precursor compositions employed should vary in terms of the electrolyte, e.g., salt, concentration. The precursor to the more conductive TTI material, for example, may further comprise at least 0.1 wt. %, e.g., at least 1.0 wt. % or at least 10 wt. % of a salt, e.g., an organic salt, to impart conductivity thereto. In terms of ranges, the precursor to the more conductive TTI material may comprise from 0.5 to 10 wt. %, e.g., from 3 to 15 wt. % or from 10 to 50 wt. % of a salt, e.g., an organic salt. Conversely, the precursor to the less conductive TTI material, for example, may comprise less than 0.01 wt. %, e.g., less than 0.1 wt. % or less than 1.0 wt. % of a salt, e.g., an organic salt.

The specific composition of the more conductive precursor, e.g., second TTI material precursor 60' that is used to form the second TTI material 60, may similarly vary widely. In an exemplary embodiment, the more conductive precursor, e.g., the second TTI material precursor 60', comprises the polymer matrix, the plasticizer, and the salt, as discussed above, but preferably further comprises a carrier medium (e.g., solvent) for imparting the desired physical properties for deposition thereof as well as solubilizing the polymer contained therein. In another embodiment, the more conductive TTI material precursor comprises a salt, a monomer and an initiator, and polymerization occurs onto the surface of the less conductive material or material precursor, e.g., through free radical polymerization, optionally with application of UV radiation. The deposition and polymerization of the first and second TTI material precursors may be conducted in any desired sequence or simultaneously, as discussed above.

The carrier medium for either precursor may comprise water or an organic solvent. As these materials are preferably microdispensed onto the contact pads 20 and 30 using microdispensing methods and equipment as described in jointly owned U.S. Pat. No. 5,554,339, previously incorporated herein by reference, similar considerations as to ingredients, viscosity, surface preparation and pretreatment and the like also apply to the present invention.

As discussed, one of the TTI materials should be more conductive than the other of the TTI materials. The second TTI material 60, for example, may be substantially conductive. For example, the second TTI material 60 preferably comprises a polymer layer (preferably a continuous polymer layer), a polymer matrix, a plasticizer, and an electrolyte (e.g., a salt). In a preferred embodiment, the second polymer layer comprises from 10 to 60 wt. %, e.g., from 20 to 40 wt. %, polymer matrix, from 40 to 90 wt %, e.g., from 60 to 80 wt. %, plasticizer, and from 0.05 to 20 wt. %, e.g., from 0.1 to 10 wt. %, salt. The polymer matrix optionally is selected from the group consisting of polyvinylchloride (PVC), polyurethane (PU), polyvinylacetate, carboxylated PVC, hydroxylated PVC and polydimethylsiloxane (silicon rubber). The plasticizer is optionally selected from the group consisting of trioctyl phosphate (TOP), nitrophenyloctyl ether (NPOE), bisethylhexylsebacate (BEHS), trimethyl trimellitate (TMTT), dioctyl adipate (DOA) and diisobutyl phthalate (DIBP).

The electrolyte, e.g., salt, selected for the conductive material is preferably highly lipophilic so as to enhance polymer solubility and can be either organic or inorganic. Exemplary organic salts may be selected from the group consisting of dodecyl sulfosuccinate, lauryl sulfate, alkyl ether phosphates, tetramethylammonium salts, benzalkonium salts, cetylpyridinium salts and zwitterionic organic salts, e.g., cocamidopropyl hydroxysultaine. Exemplary inorganic salts may be selected from the group consisting of iodide, bromide, perchlorate and zwitterionic inorganic salts. In a preferred embodiment, the salt comprises quaternary ammonium borate.

As illustrated in FIGS. 1a and 1b, as time increases from the date of manufacture of the device 10 and/or as temperature increases, the electrolyte (e.g., a salt) may diffuse 70 out of the more conductive second TTI material 60 and into the less conductive first TTI material 50 such that the conductivity of the first TTI material 50 increases over time and/or temperature. In some embodiments, a potential or potential cycle 80 may be used to take an initial measurement at the date of manufacture, which may indicate a high initial impedance value that would decrease as the electrolyte further diffuses 70 from the second TTI material 60 into the first TTI material 50 resulting in an increase in conductivity of the first TTI material 50.

Figure 1C:
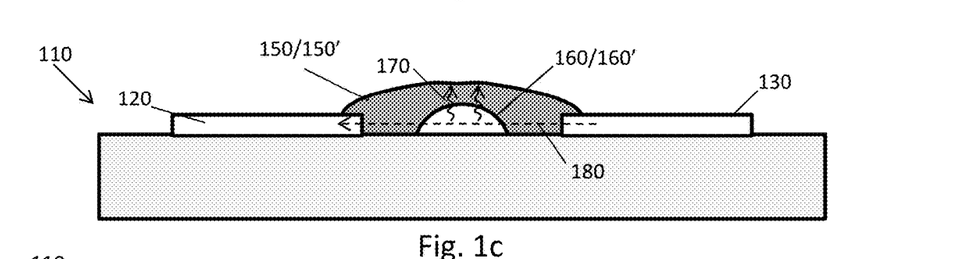
FIGS. 1c and 1d show side and plane views, respectively, of a TTI device in accordance with another embodiment of the invention.
Figure 1D:
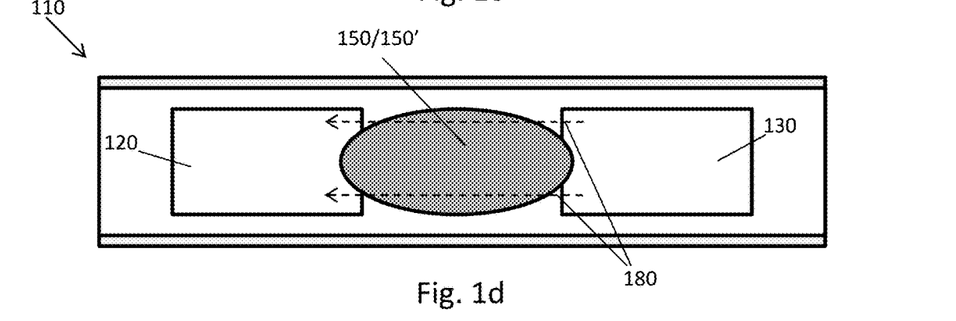

In an alternative embodiment, shown in FIGS. 1c and 1d, a first TTI material 150 may be formed by depositing a first TTI material precursor 150' between contact pads 120 and 130 and over a second TTI material 160 or second TTI material precursor 160'. Preferably, the first TTI material is more conductive than the second TTI material, although the reverse is also contemplated. In accordance with this aspect, the second TTI material 160 may be formed prior to formation of the first TTI material 150 by depositing a second TTI material precursor 160' between the contact pads 120 and 130 on a surface of TTI device 110. Preferably, the second TTI material precursor 160' is deposited not in contact with the contact pads 120 and 130. The second TTI material 160 may comprise a polymer layer that includes a conductive material, e.g., a salt, and the second TTI material precursor 160' may comprise a polymer layer precursor and the electrolyte. For example, the second TTI material 160 may be formed by depositing, e.g., printing, and drying and/or curing the second TTI material precursor 160', e.g., polymer layer precursor, onto a surface of the TTI device 110 so that the second TTI material precursor 160' does not contact the contact pads 120 and 130, e.g., an amperometric channel pad and a Hct pad or two Hct pads.

Preferably, the first TTI material precursor 150' is deposited over the second TTI material or the second TTI material precursor and in contact with contact pads 120 and 130. The first TTI material 150 may comprise a polymer layer and the first TTI material precursor 150' may comprise a polymer layer precursor. For example, the first TTI material 150 may be formed by depositing, e.g., printing, drying and/or curing the first TTI material precursor 150', e.g., polymer layer precursor, between and preferably overlapping contact pads 120 and 130, e.g., an amperometric channel pad and a Hct pad or two Hct pads, such that the first TTI material precursor 150' substantially covers the second TTI material 160 or the second TTI material precursor 160'.

In one aspect, the first TTI material precursor 150' and the second TTI material precursor 160' are treated, e.g., with heat or other radiation, dried and/or cured, together or separately, to form the first TTI material 150 and the second TTI material 160 respectively. In this manner, a heterogeneous layer is formed in a region between contact pads 120 and 130, and preferably overlapping the contact pads 120 and 130, so that the first TTI material 150 contacts at least a portion of the first and second contact pads and the second TTI material 160 does not contact either contact pad.

As illustrated in FIGS. 1c and 1d, as time and/or temperature increases, the electrolyte (e.g., a salt) may diffuse 170 out of the substantially conductive second TTI material 160 and into the substantially non-conductive first TTI material 150, such that the first TTI material 150 increases in conductivity. A potential or potential cycle 180 may be used in measuring an electrical property associated with the heterogeneous layer, e.g., the first and second TTI materials 150 and 160, as the electrolyte diffuses 170 out of the second TTI material 160 and into the first TTI material 150, thereby increasing the conductivity of the first TTI material 150.

Figure 1E:
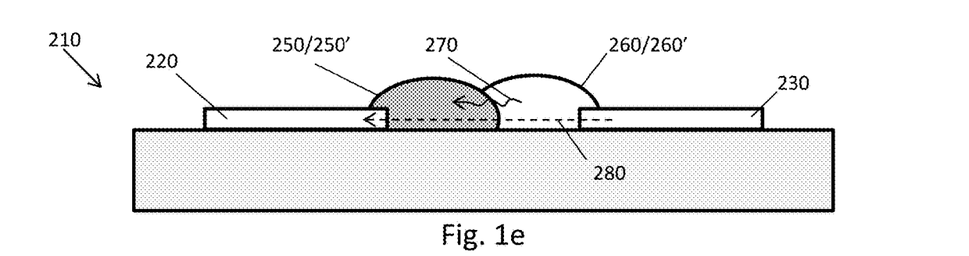
FIGS. 1e and 1f show side and plane views, respectively, of a TTI device in accordance with another embodiment of the invention.
Figure 1F:
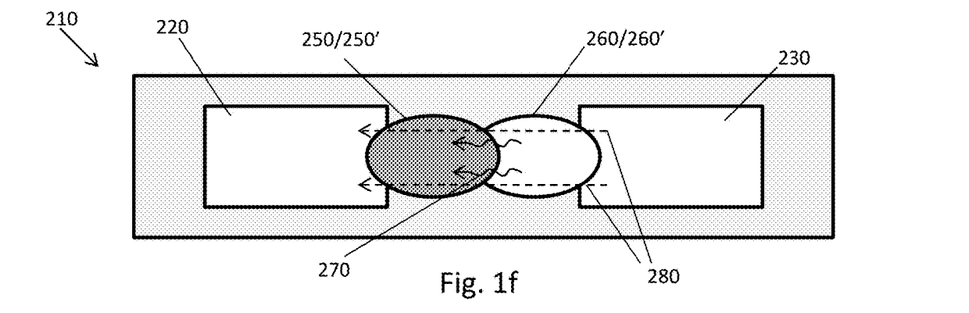

In another embodiment, shown in FIGS. 1e and 1f, a first TTI material 250 may be formed by depositing a first TTI material precursor 250' between contact pads 220 and 230, but in contact with only one of the contact pads. Thus, the first TTI material precursor 250' may be deposited in contact with only one of the contact pads 220 and 230 and forming a space between the TTI material precursor 250' and the other of the two contact pads 220 and 230. The first TTI material precursor may then be dried and/or cured to form the first TTI material. As shown, first TTI material 250 contacts contact pad 220, but is not in electrical contact with contact pad 230.

The second TTI material 260 may be formed by depositing a second TTI material precursor 260' between contact pads 220 and 230, but in contact with the first TTI material 250 or first TTI material precursor 250' and the contact pad that is not in contact with first TTI material 250 or first TTI material precursor 250'. The second TTI material precursor may then be dried and/or cured to form the second TTI material. As described above, the second TTI material 260 preferably is more conductive than the first TTI material 250, although the reverse is also contemplated. The first and second TTI precursors may be treated, dried and/or cured, e.g., with heat or other radiation, separately or simultaneously, to form the first TTI material 250 and the second TTI material 260, respectively, and thereby forming a heterogeneous layer.

As illustrated in FIGS. 1e and 1f, as time and/or temperature increases, the electrolyte (e.g., a salt) may diffuse 270 out of the substantially conductive second TTI material 260 and into the substantially non-conductive first TTI material 250 such that the conductivity of the first TTI material 250 increases. A potential or potential cycle 280 may be used in measuring an electrical property associated with the first and second TTI materials 250 and 260 as the electrolyte diffuses 270 out of the second TTI material 260 and into the first TTI material 250 in order to determine device usability.

Figure 1G:
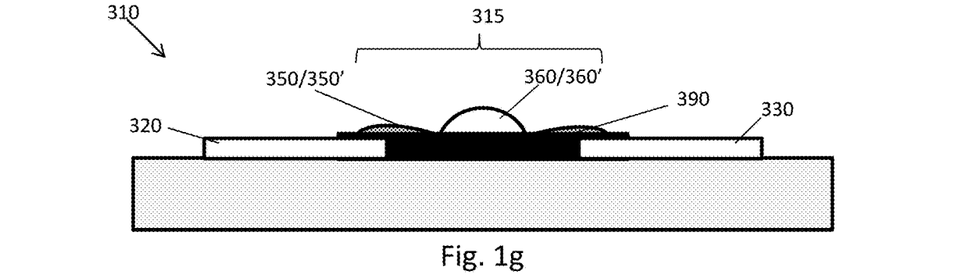
FIGS. 1g and 1h show side and plane views, respectively, of a TTI device with a boundary structure in accordance with another embodiment of the invention.
Figure 1H:
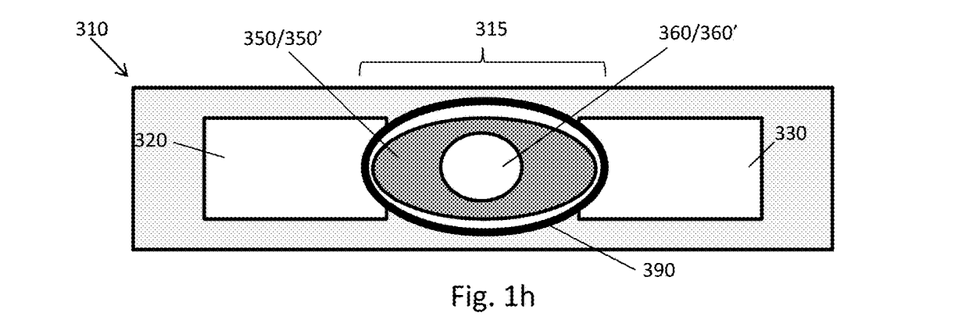

The first and second TTI materials preferably are accurately positioned in the devices in order, for example, to avoid potential contamination of the connector, e.g., connector pins, in the instrument. Notably, the transfer of polymeric material from the first and second TTI materials to the connector pins should be minimized or avoided. Consequently, in some aspects, as shown in FIGS. 1g and 1h, the present invention also relates to devices 310 having a boundary structure 390 that facilitates controlling the spreading of the dispensed first and second precursors 350' and 360' that form the first and second TTI materials 350 and 360, e.g., the heterogeneous layer 315. The boundary structure 390 may, for example, be positioned at a predetermined region of the device 310, for example as a polygon, e.g., square, pentagon, hexagon, octagon, and the like, or as a cylindrical or ring shape. This boundary structure 390, if employed, preferably is positioned in a manner that intersects the two adjacent pads 320 and 330.

The boundary structure 390 may be formed, for example, by patterning a ridge of passivation material, e.g., a photoformable passivation material, such as a photoformable polyimide. The photoformable passivation material may be spin-coated and patterned to form an insulating layer over the contact lines on the chip. Thus, the mask for that process may also include the ring structures. Jointly owned U.S. Pat. No. 5,200,051, the entirety of which is incorporated by reference, discloses similar processes and photoformable materials. Other photoformable materials, e.g., those based on polyvinyl alcohol or dichromated gelatin, may also be used.

Figure 2:
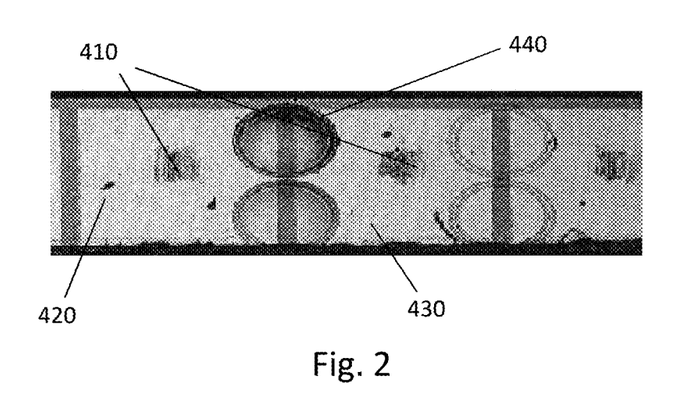
FIG. 2 presents an image showing a TTI device deposited on first and second electrical pads in accordance with aspects of the invention.

In the above-described embodiments, connector pin tips may initially contact a top portion of the contact pads and move slightly towards a middle of the chip as a connector applies more force. Accordingly, it is preferred that the boundary structure 390, e.g., ring, be used for first and second TTI material positions that are closer to the middle of the chip in order to properly locate the heterogeneous layer. In this manner, the TTI material preferably is positioned beyond the extent of travel of the pin tip, thus obviating the contamination issue. For example, the scratch marks 410 in the middle of the contact pads 420 and 430 in FIG. 2 show where the connector pins have hit the contact pads and moved during connector engagement in relationship to boundary structure 440.

In the above-described embodiments, the step of depositing, e.g., printing, the first and second TTI material precursors between the two contact pads may be accomplished by using a microdispensing process such as the one described in jointly owned U.S. Pat. No. 5,554,339, the entirety of which is incorporated herein by reference. This process involves preparing a fluid composition suitable for forming the polymer layer and loading it into a microsyringe assembly. The microsyringe assembly may comprise, for example, a reservoir, a microsyringe needle, a pump for delivering the TTI material precursor from the reservoir to the microsyringe needle, and a multidirectional controller so that droplets may be brought into contact with the area between the contact pads. Automatic alignment of the needle tip to the dispensing location may be achieved in manufacturing, for example, using an optical recognition system using one or more fiduciary marks.

In a preferred embodiment, particularly for low-cost compatible manufacturing methods, the process of depositing the TTI material precursor may be substantially similar to the printing process that is employed for the manufacture of sensing membranes onto electrodes (see, e.g., U.S. Pat. No. 5,554,339) and the printing of reagents onto surfaces or conduit walls of cartridge components for subsequent dissolution into a blood sample.

As described above, the heterogeneous layer is preferably formed by microdispensing one or more drops of the first and second TTI material precursors onto the TTI device and removing the carrier medium, optionally with heat, and/or drying the precursor to form the first and second TTI materials. In a preferred embodiment, e.g., for the embodiments described herein, the deposited first and second TTI material precursors form a substantially circular shape having a diameter in the range of from about 20 μm to about 2 mm, preferably 100 μm to 500 μm, and are generally domed, covering, as required, the distance between the two pads, which preferably is in the range of from about 10 µm to 1 mm, preferably from about 10 µm to 200 µm. The average thickness of the heterogeneous layer is generally in the range of from about 1 µm to about 200 µm, preferably from about 20 µm to about 60 µm. One skilled in the art will appreciate that ranges outside of those provided above may be employed, for example, for larger sensor devices such as some home use glucose testing strips.

The above-described configurations of a TTI device enable a reader instrument (e.g., an analyzer) to measure an electrical property of the first and second TTI materials before any sample or calibrant fluid contacts the electrodes, which are located in a fluid conduit within the cartridge. See, for example, jointly owned U.S. Pat. Nos. 5,096,669 and 7,491,821, the entireties of which are incorporated herein by reference. In embodiments, the electrical property measured may include current, resistance, impedance, conductivity, or a combination thereof. In a preferred embodiment, the electrical property that is measured is the open circuit resistance ($R_{TTI}$) of the first and second TTI materials. If the electrical property, e.g., $R_{TTI}$ measurement, does not exceed a predetermined threshold value or is within a certain range, the cartridge is considered valid for use. For such cartridges, depending on how an analyzer is programmed, the analyzer may indicate that the cartridge has expired or otherwise reject the cartridge and abort the test cycle, or engage in another remedial action, e.g., sensor output correction, as discussed in greater detail herein. Nevertheless, it should be understood, however, that such devices may still be suitable for use but may not have the desired degree of clinical precision.

The present invention advantageously avoids the need to add conductive particles, e.g., carbon black, conductive carbon nanotubes, metallic particles, metallic oxide, semiconductor particles, etc, to the first and second TTI materials in order to adjust an initial resistivity of the heterogeneous layer to a desired level. By contrast, the present invention, in some aspects, relies on the second TTI material comprising a polymer, e.g., a conductive material, and various other molecular species (e.g., an electrolyte). While these other molecular species may be polar or ionic and thus affect the substantial conductivity of the second TTI material, they are not particulate in nature. In a preferred embodiment, lipophilic organic ammonium ion salts are used, e.g., dodecylammonium chloride and tetraphenylborate to impart the desired degree of resistivity/conductivity. Nevertheless, in other aspects of the invention, such conductive particles may be included in the conductive TTI material or conductive TTI material precursor used in the devices and methods of the invention.

While the present invention is conceived in a first embodiment as a process for determining device usability, in a second embodiment, the invention may be used for sensor correction. Thus, in the first embodiment, for example, the invention is to a TTI device configured for determining device usability comprising first and second TTI materials, e.g., a heterogeneous layer, formed on a surface of the TTI device, wherein the surface comprises two adjacent electrical contact pads. As indicated above, the first and second TTI materials preferably cover at least a portion of the two electrical contact pads and at least a portion of the space on the surface between the contact pads. In a preferred embodiment, a preselected potential or potential cycle is applied to the pads and the impedance (Z) or current (I) associated with the (combined) first and second TTI materials as a heterogeneous layer is measured, and the resulting measured value is compared with a predetermined threshold value to determine whether the device is usable.

The invention may also be used to determine the average shelf life of similarly aged and stored devices, e.g., devices from the same manufacturing lot. Thus, in another embodiment, the invention is to a device having a usability threshold and including a sensor and first and second TTI materials, e.g., included in a heterogeneous layer, formed on a surface of a TTI device, wherein the surface may be substantially planar and comprises two adjacent electrical contact pads having a space therebetween. The first and second TTI materials cover at least a portion of the two electrical contact pads and a portion of the space on the surface between the contact pads. In operation, a preselected potential or potential cycle is applied to the contact pads and an electrical property, e.g., impedance or current, associated with the first and second TTI materials is measured. The measured value is converted to a value indicative of an average shelf life time remaining for other devices from the same manufacturing lot as the device signal from the output of the sensor to provide a corrected sensor signal.

In a related embodiment, the invention is to a method of correcting a signal in a sensing device, comprising the steps of: (a) providing a sensing device comprising a sensor, a first electrical pad, a second electrical pad, and first and second TTI materials, e.g., included in a heterogeneous layer, contacting at least a portion of the first and second electrical pads; (b) applying a potential across the first and second electrical pads; (c) measuring an electrical property associated with the first and second TTI materials (heterogeneous layer); (d) determining a correction factor associated with the measured electrical property, e.g., from a look up table or the like; and (e) applying the correction factor to a signal generated by the sensor to produce a corrected signal.

In order to determine the appropriate correction factor, e.g., from a look up table or correction algorithm, it is necessary to establish a relationship between the electrical property and the correction factors. Thus, in another embodiment, the invention is to a method of determining a correction factor comprising the steps of: (a) providing a plurality of devices, each of the devices comprising a sensor; a first electrical pad; a second electrical pad; and a heterogeneous layer contacting at least a portion of the first and second electrical pads, wherein the devices have been exposed to different environmental conditions; (b) measuring an electrical property of the heterogeneous layer for each of the devices; (c) measuring a sensor signal for a control fluid, as defined below, for each of the devices; and (d) correlating the measured electrical properties with the measured sensor signals for the plurality of devices to determine the correction factor.

In a more generalized embodiment, the invention is to a device having first and second TTI materials, e.g., included in a heterogeneous layer, formed on a surface, wherein the surface comprises two adjacent electrical contact pads. The first and second TTI materials cover at least a portion of the two electrical contact pads and a portion of the space on the surface between the pads. When a preselected potential or potential cycle is applied to the two contact pads and an electrical property, e.g., impedance or current, associated with the first and second TTI materials is measured, the measured value determines whether the device is usable and, if the device is usable, whether it is necessary to correct the signal. If it is necessary to correct the signal, the device may determine the appropriate correction factor and modify a sensor signal from the device based on the correction factor to provide a corrected signal. For example, a portion of a manufacturing lot of devices can be tested under different storage conditions and tested with a standard liquid of known composition (control fluid). If the TTI value and control fluid values are recorded, any variation between the expected and measured control fluid value can be correlated with the TTI value and a correction algorithm created. This can then be implemented in the instrument when running real samples with that manufacturing lot of devices.

In accordance with aspects of the invention, various potential cycles may be used in measuring the electrical property associated with the first and second TTI materials, e.g., the heterogeneous layer. In some exemplary embodiments, the potential cycle may be selected from a sigmoidal potential cycle, a fixed applied potential, and a potential that is a sequence of fixed applied potential steps. Measurements may be made, for example, with an impedance measuring circuit in an instrument, or a current measuring circuit in an instrument. In one embodiment, an initial current value associated with the heterogeneous layer is measured when the device is manufactured and the threshold level is at least three times, preferably at least five times, greater than the initial current value. Conversely, in another aspect, an initial impedance value associated with the heterogeneous layer is measured when the device is manufactured and the threshold level is at least three times less, preferably at least five times less, than the initial impedance. In some exemplary embodiments where current is measured, the current ranges from picoamps to milliamps, but more typically from nanoamps to microamps, e.g., from 0.1 to 100 nanoamps. Where impedance is measured, the typical impedance may range, for example, from below the megaohm range to above the gigaohm range, more typically in the tens of megaohms to low gigaohm range, optionally from 100 to 1500 megaohms at a frequency of from about 1 to about 10 Hz.

Where a sensor correction is made, the correction value may be selected from an amperometric correction value, a potentiometric correction value, a coulombic correction value and a conductivity correction value. These values are typically applied to a sensor selected from the group consisting of a pH sensor, oxygen sensor, carbon dioxide sensor, hematocrit sensor, glucose sensor, lactate sensor, creatinine sensor, sodium sensor, potassium sensor, magnesium sensor, calcium sensor, chloride sensor, phosphate sensor, liver enzyme sensor, BNP sensor, troponin sensor, BUN sensor, CKMB sensor, NGAL sensor, TSH sensor, D-dimer sensor, PSA sensor, PTH sensor, cholesterol sensor, ALT sensor, AST sensor, prothrombin sensor, APTT sensor, ACT sensor, galectin sensor, and combinations thereof.

The present invention may be easily adaptable to widely available commercial technologies and can be performed with existing electronics that require no hardware changes but only a software modification, which are generally simpler to implement than hardware modifications. For example, an i-STAT instrument may be able to measure conductivity at 10 kHz and 50 kHz, but may be conveniently expanded to a wider frequency range. In a preferred embodiment, this circuitry is programmed to measure the electrical resistance between adjacent contact pads at a frequency of 10 Hz. It is believed that low frequency impedance measurements in the range of from about 1 Hz to about 100 Hz are most sensitive in detecting a change in the electrical property of the heterogeneous layer. Without being bound by theory, it is understood that changes in circuit impedance may be due to a change in the bulk membrane resistance, which is best observed when the ions in the membrane migrate some distance so they must be under a polarizing voltage for some time, which requires a low frequency. One possible mechanism is that at higher frequencies, the voltage oscillates so quickly that the ions do not migrate appreciably. As a result, the resistance to their movement does not influence the impedance. Another possibility is that the impedance change over time that is observed in the present invention may be contributed in part by the electrode oxidation and its interface with the bulk polymer membrane. In general, electrode polarization impedance becomes more significant at lower frequencies than at higher frequencies. In any event, an important parameter to the present invention is an empirically observable and consistently predictable change in the electrical property.

To avoid compromising the use of the contact pads for their primary function, typically analyte sensing, where the electrical property that is measured is the open circuit resistance, the $R_{TTI}$ preferably is much greater than, e.g., at least 1000 times greater than, the closed circuit resistance, i.e., the resistance measured between the electrodes attached to the contact pads with either sample or calibrant fluid covering the electrodes. However, the $R_{TTI}$ preferably is much lower, e.g., at least 100 times lower, than the existing open circuit resistance, i.e., the resistance between the contact pins prior to contacting the pads. This goal may be accomplished through careful design of the geometry of the heterogeneous layer and control of the first and second TTI material compositions. Thus, a reduced cross-sectional polymer layer area and an extended polymer path length between the pads will generally lead to an increased resistance for any given material composition, whereas increasing the ionic content and ion mobility of the polymer layer for a given geometry will generally lead to a decreased resistance. Note that the typical sample or calibrant fluid resistance is in the range of about ten to thousands of ohms, whereas the open circuit resistance is generally greater than several giga-ohms. Thus, the TTI resistance is preferably in the mega-ohm to low giga-ohm range.

In embodiments, a quantitative relationship between $R_{TTI}$ and actual aging of a test cartridge is established. As indicated herein, the objective is to prevent expired cartridges from being used and prevent usable cartridges from being discarded. Thus, in another embodiment, the invention is to a method of determining a threshold level associated with analytical device usability. The method comprises the steps of: (a) providing a plurality of devices, each of the devices comprising a sensor; a first electrical pad; a second electrical pad; and a heterogeneous layer contacting at least a portion of the first and second electrical pads, wherein the devices have been exposed to different environmental conditions; (b) measuring an electrical property of the heterogeneous layer for each of the devices; (c) measuring a sensor signal for a control fluid for each of the devices; (d) identifying a subset of the plurality of devices that provide a signal having a predetermined acceptable precision level for the control fluid; and (e) determining the threshold level that corresponds to the electrical property of the heterogeneous layer for the subset of the plurality of devices.

In accordance with aspects of the invention, the invention has the advantage that it enables a sensor that would otherwise have been considered to have exceeded its shelf life to still be used based on a time and temperature integrated correction factor. For example, once the TTI relationship between thermal exposure (or other environmental conditions) and change in electrical property, e.g., impedance, has been established, a dynamic correction algorithm can be created and embedded into the instrument software to generate the correction factor.

An approach to correcting an assay result for aging may rely upon the following. The assay and TTI need to predictably change when subjected to the same thermal stress independent of the conditions to which it has been subjected. For example, an assay storage condition with highly fluctuating temperature (bounded by the allowable extremes) should produce nearly the same change as is observed when the assay is stored at a fixed temperature. If this condition is met, and if the time and mean kinetic temperature (MKT), which is the equivalent fixed temperature at which an assay would need to be held to reach the same degree of aging, are known then the assay result can be corrected. If the duration of thermal stress is known (ideally the time since the date of manufacture), the TTI can be used to calculate the MKT. Based upon the relationship established between the MKT and the change in the assay result, the expected change can be back calculated from the result. The correction algorithm may be derived using an Arrhenius model. For example, a correction factor for creatinine may be determined by the following formula:

$$[Crea] = b * response - c$$

wherein:

"response" is a slope of the sensor response (e.g., current) for the sample;

(b) is a calibration parameter for slope (b) of the sensor response;

(c) is a calibration parameter for intercept (c).

With aging, the response slope b is changing according to Arrhenius model and creatinine concentration can be corrected as follows:

$$[CREA] = \frac{b}{\theta_1 \cdot \exp\left(-\left(\theta_2 \cdot \exp\left(-\frac{Ea_{CREA}}{R} \cdot \left(\frac{1}{MKT} - \frac{1}{T_{ref}}\right)\right)\right) \cdot time\right) + \theta_3} \times Response + c$$

wherein:

MKT is the mean kinetic temperature and can be estimated from the measured TTI impedance $R_{TTI}$;

$Ea_{CREA}$ is apparent activation energy for change in creatinine sensor response;

R is the universal gas constant;

$T_{ref}$ is the experimental reference temperature;

$\theta_1$ is a pre-exponential factor for time/temperature changes in b;

$\theta_2$ is the rate of change in b at $T_{ref}$; and $\theta_3$ is non-temperature dependent offset=$1-\theta_1$.

By utilizing the present invention it is possible to significantly further extend the time available for typical room temperature storage of blood testing devices. In this context, the improvement can be at least about 50%. In addition, the invention may be applied to any electrochemical test device where the instrumentation enables current or impedance measurements, e.g., glucose meters used for diabetes monitoring with electrochemical sensor strips. The invention also simplifies the process of implementing point of care testing technology for the user, e.g., nurse, doctor or other healthcare professional. It also ensures that test devices, e.g., cartridges, strips and the like, have been stored properly prior to the use of each individual device. It can be used to compensate for device aging factors and improve the accuracy of results throughout the life of the device.

In another embodiment of the present invention, the measured value from the TTI is used to calculate the remaining percentage of thermal stress (or other environmental stressors) for the rest of a manufacturing lot of the same devices stored under the same conditions. This is essentially the length of time for room temperature storage that remains for all of the other devices that were stored with the tested device but have yet to be used. As all of the devices in a given lot (e.g., a given i-STAT cartridge manufacturing lot) are manufactured in the same way and at the same time, the tested device gives a measured impedance or current value that not only is relevant to that particular device (as applied in other disclosed embodiments) but can also be used predicatively with respect to other devices from the same manufactured lot that have been subjected to the same storage conditions as the tested device.

For example, assuming a thermal stress budget of 100% at the time the lot of cartridges are removed from refrigeration, at the time a particular cartridge is tested, it is possible to calculate from the measured TTI value that some fraction of the budget remains, i.e., a value from 100% to 0% (expiry). This is based on an embedded data curve reflecting this range that is part of the instrument software algorithm. The curve is derived from the type of data shown in the various figures, i.e., factory determined and uploaded to the instrument for predetermined lots.

Optionally, this information is displayed on the instrument and relayed to the hospital's point of care coordinator. This enables a new supply of devices, e.g., a new box of cartridges, to be ordered when expiry is imminent. It also enables the creation of a cartridge management report that allows the point of care coordinator to easily monitor and manage cartridges throughout a facility in a remote manner. Note that in practice, individual cartridges are generally traceable to a particular box and it is a reasonable assumption that cartridges are stored together in the box. Consequently, every time a cartridge is run from a particular box it provides useable information on the amount of room temperature storage for the remaining cartridges in that box and all boxes stored similarly.

While the invention has been described in terms of various preferred embodiments, those skilled in the art will recognize that various modifications, substitutions, omissions and changes can be made without departing from the spirit of the present invention. Accordingly, it is intended that the scope of the present invention be limited solely by the scope of the following claims.

What is claimed is:

1. A method of applying a correction factor to a signal, comprising the steps of:

providing a device comprising: a first electrical pad; a second electrical pad; a first polymer layer contacting the first electrical pad and the second electrical pad; and a second polymer layer contacting the first polymer layer and not the first electrical pad and the second electrical pad, wherein the first polymer layer comprises a polymer matrix and a plasticizer, and wherein the second polymer layer comprises a polymer matrix, a plasticizer, and an organic salt;

obtaining an initial current value associated with the first polymer layer and the second polymer layer that is measured when the device is manufactured, wherein a usability threshold level of the device is at least five times greater than the initial current value;

applying a potential across the first electrical pad and the second electrical pad;

measuring an electrical property associated with the first polymer layer and the second polymer layer based on the potential applied, wherein the measured electrical property predictably changes over time based on exposure of the device to environmental conditions, and wherein the electrical property comprises current, resistance, impedance, conductivity, or a combination thereof;

determining whether the electrical property exceeds the usability threshold level;

when the electrical property does not exceed the usability threshold level, determining the correction factor associated with the measured electrical property; and applying the correction factor to the signal generated by a sensor to produce a corrected signal.

2. The method of claim 1, wherein the correction factor is selected from a group consisting of an amperometric correction value, a potentiometric correction value, a coulombic correction value and a conductivity correction value.

3. The method of claim 1, wherein the sensor is selected from a group consisting of a pH sensor, an oxygen sensor, a carbon dioxide sensor, a hematocrit sensor, a glucose sensor, a lactate sensor, a creatinine sensor, a sodium sensor, a potassium sensor, a chloride sensor, a calcium sensor, a BNP sensor, a troponin sensor, a CKMB sensor, a NGAL sensor, a TSH sensor, a D-dimer sensor, a PSA sensor, a PTH sensor, a cholesterol sensor, an ALT sensor, an AST sensor, a prothrombin sensor, an APTT sensor, an ACT sensor and a galectin sensor.

4. The method of claim 1, wherein the potential comprises a sigmoidal potential cycle, a fixed applied potential, a sequence of fixed applied potential steps, or a combination thereof.

5. The method of claim 1, wherein the potential comprises a potential cycle that is applied at a predetermined frequency in the range of about 1 Hz to about 100000 Hz.

6. The method of claim 1, further comprising inserting the device into an analyzer configured to determine whether the measured electrical property associated with the first polymer layer and the second polymer layer has exceeded the usability threshold level of the device.

7. A method of applying a correction factor to a signal, comprising the steps of:

providing a device comprising: a first electrical pad; a second electrical pad; a first polymer layer contacting the first electrical pad and the second electrical pad; and a second polymer layer contacting the first polymer layer and not the first electrical pad and the second electrical pad, wherein the first polymer layer comprises a polymer matrix and a plasticizer, and wherein the second polymer layer comprises a polymer matrix, a plasticizer, and an organic salt;

obtaining an initial current value associated with the first polymer layer and the second polymer layer that is measured when the device is manufactured, wherein a usability threshold level of the device is at least five times less than the initial current value;

applying a potential across the first electrical pad and the second electrical pad;

measuring an electrical property associated with the first polymer layer and the second polymer layer based on the potential applied, wherein the measured electrical property predictably changes over time based on exposure of the device to environmental conditions, and wherein the electrical property comprises current, resistance, impedance, conductivity, or a combination thereof;

determining whether the electrical property exceeds the usability threshold level;

when the electrical property does not exceed the usability threshold level, determining the correction factor associated with the measured electrical property; and applying the correction factor to the signal generated by a sensor to produce a corrected signal.

8. A method of applying a correction factor to a signal, comprising the steps of:

providing a device comprising a first electrical pad; a second electrical pad; a first polymer layer contacting at least a portion of the first electrical pad; and a second polymer layer contacting at least a portion of the second electrical pad and at least a portion of the first polymer layer, wherein the first polymer layer comprises a polymer matrix and a plasticizer, and wherein the second polymer layer comprises a polymer matrix, a plasticizer, and an organic salt;

obtaining an initial current value associated with the first polymer layer and the second polymer layer that is measured when the device is manufactured, wherein a usability threshold level of the device is at least five times greater than the initial current value;

applying a potential across the first and the second electrical pads;

measuring an electrical property associated with the first and the second polymer layers based on the potential applied, wherein the measured electrical property predictably changes over time based on exposure of the device to environmental conditions, and wherein the electrical property comprises current, resistance, impedance, conductivity, or a combination thereof;

determining whether the electrical property exceeds the usability threshold level;

when the electrical property does not exceed the usability threshold level, determining the correction factor associated with the measured electrical property; and applying the correction factor to the signal generated by a sensor to produce a corrected signal.

9. The method of claim 8, wherein the correction factor is selected from a group consisting of an amperometric correction value, a potentiometric correction value, a coulombic correction value and a conductivity correction value.

10. The method of claim 8, wherein the sensor is selected from a group consisting of a pH sensor, an oxygen sensor, a carbon dioxide sensor, a hematocrit sensor, a glucose sensor, a lactate sensor, a creatinine sensor, a sodium sensor, a potassium sensor, a chloride sensor, a calcium sensor, a BNP sensor, a troponin sensor, a CKMB sensor, a NGAL sensor, a TSH sensor, a D-dimer sensor, a PSA sensor, a PTH sensor, a cholesterol sensor, an ALT sensor, an AST sensor, a prothrombin sensor, an APTT sensor, an ACT sensor and a galectin sensor.

11. The method of claim 8, wherein the potential comprises a sigmoidal potential cycle, a fixed applied potential, a sequence of fixed applied potential steps, or a combination thereof.

12. The method of claim 8, wherein the potential comprises a potential cycle that is applied at a predetermined frequency in the range of about 1 Hz to about 100000 Hz.

13. The method of claim 8, further comprising inserting the device into an analyzer configured to determine whether the measured electrical property associated with the first and the second polymer layers has exceeded the usability threshold level of the device.

14. A method of applying a correction factor to a signal, comprising the steps of:

providing a device comprising a first electrical pad; a second electrical pad; a first polymer layer contacting at least a portion of the first electrical pad; and a second polymer layer contacting at least a portion of the second electrical pad and at least a portion of the first polymer layer, wherein the first polymer layer comprises a polymer matrix and a plasticizer, and wherein the second polymer layer comprises a polymer matrix, a plasticizer, and an organic salt;

obtaining an initial current value associated with the first polymer layer and the second polymer layer that is measured when the device is manufactured, wherein a usability threshold level of the device is at least five times less than the initial current value;

applying a potential across the first electrical pad and the second electrical pad;

measuring an electrical property associated with the first polymer layer and the second polymer layer based on the potential applied, wherein the measured electrical property predictably changes over time based on exposure of the device to environmental conditions, and wherein the electrical property comprises current, resistance, impedance, conductivity, or a combination thereof;

determining whether the electrical property exceeds the usability threshold level;

when the electrical property does not exceed the usability threshold level, determining the correction factor associated with the measured electrical property; and applying the correction factor to the signal generated by a sensor to produce a corrected signal.

* * * * *